United States Patent
Van Bommel et al.

(10) Patent No.: US 12,285,550 B2
(45) Date of Patent: Apr. 29, 2025

(54) LED FILAMENT FOR DISINFECTION

(71) Applicant: SIGNIFY HOLDING B.V., Eindhoven (NL)

(72) Inventors: Ties Van Bommel, Horst (NL); Rifat Ata Mustafa Hikmet, Eindhoven (NL)

(73) Assignee: SIGNIFY HOLDING B.V., Eindhoven (NL)

( * ) Notice: Subject to any disclaimer, the term of this patent is extended or adjusted under 35 U.S.C. 154(b) by 0 days.

(21) Appl. No.: 18/580,670

(22) PCT Filed: Jun. 23, 2022

(86) PCT No.: PCT/EP2022/067233
§ 371 (c)(1),
(2) Date: Jan. 19, 2024

(87) PCT Pub. No.: WO2023/001484
PCT Pub. Date: Jan. 26, 2023

(65) Prior Publication Data
US 2024/0366825 A1 Nov. 7, 2024

(30) Foreign Application Priority Data

Jul. 19, 2021 (EP) ................................. 21186326

(51) Int. Cl.
*A61L 9/20* (2006.01)
*F21K 9/232* (2016.01)
(Continued)

(52) U.S. Cl.
CPC ............... *A61L 9/20* (2013.01); *F21K 9/232* (2016.08); *A61L 2209/12* (2013.01);
(Continued)

(58) Field of Classification Search
CPC .................................. A61L 9/20; F21K 9/232
(Continued)

(56) References Cited

U.S. PATENT DOCUMENTS 11,892,127 B2 * 2/2024 Jiang ........................ F21K 9/61
2005/0253533 A1 * 11/2005 Lys ....................... F21V 23/003
315/291
(Continued)

FOREIGN PATENT DOCUMENTS

CN 105822909 A 8/2016
CN 206076229 U 4/2017
(Continued)

*Primary Examiner* — Bryon T Gyllstrom

(57) ABSTRACT

The present invention relates to a light-emitting diode (LED) filament (1) configured to provide LED filament light and comprising an elongated carrier (2) comprising a first surface (3) and a second surface (3') arranged opposite to the first surface (3). The LED filament (1) further comprises a plurality of first light-emitting diodes (4). LEDs, distributed along the first surface (3) of the elongated carrier (2), the plurality of first LEDs (4) being configured to emit a first LED light having a dominant peak wavelength within a first wavelength range, and a plurality of second light-emitting diodes (5), LEDs, distributed along the second surface (3') of the elongated carrier (2), the plurality of second LEDs (5) being configured to emit a second LED light having a dominant peak wavelength within a second wavelength range being different from the first wavelength range. The first wavelength range is in the visible wavelength range and the second wavelength range is in the UV wavelength range and/or violet wavelength range.

13 Claims, 2 Drawing Sheets

(51) Int. Cl.
  *F21Y 107/30* (2016.01)
  *F21Y 107/70* (2016.01)
  *F21Y 107/90* (2016.01)
  *F21Y 113/00* (2016.01)
  *F21Y 113/13* (2016.01)
  *F21Y 115/10* (2016.01)

(52) U.S. Cl.
  CPC ....... *F21Y 2107/30* (2016.08); *F21Y 2107/70* (2016.08); *F21Y 2107/90* (2016.08); *F21Y 2113/13* (2016.08); *F21Y 2113/30* (2023.05); *F21Y 2115/10* (2016.08)

(58) Field of Classification Search
  USPC .......................................... 362/231
  See application file for complete search history.

(56) References Cited

U.S. PATENT DOCUMENTS

| | | | |
|---|---|---|---|
| 2008/0008620 A1* | 1/2008 | Alexiadis | F21S 4/26 422/186.3 |
| 2017/0130906 A1* | 5/2017 | Jiang | H01L 33/62 |
| 2017/0227169 A1* | 8/2017 | Jiang | F21V 3/02 |
| 2018/0180226 A1 | 6/2018 | Van Bommel et al. | |
| 2018/0328543 A1* | 11/2018 | Bergmann | H05B 45/3577 |
| 2019/0139943 A1 | 5/2019 | Tiwari et al. | |
| 2021/0381657 A1* | 12/2021 | Xiong | H01L 25/0753 |
| 2022/0202972 A1* | 6/2022 | Chen | F21V 33/0064 |
| 2022/0221112 A1* | 7/2022 | Van Bommel | F21K 9/232 |

FOREIGN PATENT DOCUMENTS

| | | |
|---|---|---|
| CN | 111029452 A | 4/2020 |
| WO | 2017181751 A1 | 10/2017 |
| WO | 2020260197 A1 | 12/2020 |
| WO | 2021063902 A1 | 4/2021 |
| WO | 2021094257 A1 | 5/2021 |

* cited by examiner

LED FILAMENT FOR DISINFECTION

CROSS-REFERENCE TO PRIOR APPLICATIONS

This application is the U.S. National Phase application under 35 U.S.C. § 371 of International Application No. PCT/EP2022/067233, filed on Jun. 23, 2022, which claims the benefit of European Patent application Ser. No. 21/186, 326.1, filed on Jul. 19, 2021. These applications are hereby incorporated by reference herein.

TECHNICAL FIELD

The present invention relates to a light emitting diode (LED) filament emitting LED filament light and disinfecting light, and to a lighting device comprising such a LED filament.

BACKGROUND

The use of light emitting diodes, LEDs, for illumination purposes continues to attract attention. Compared to incandescent lamps, fluorescent lamps, neon tube lamps, etc., LEDs provide numerous advantages such as longer operational life, reduced power consumption, and increased efficiency related to the ratio between light energy and heat energy. For this reason, incandescent lamps are rapidly being replaced by LED based lighting solutions. It is nevertheless appreciated and desired by users to have LED based light sources which resemble an incandescent bulb. For this purpose, it is possible to make use of the infrastructure for producing incandescent lamps based on glass and replace the filament with LEDs. One of the concepts is based on LED filaments placed in such a bulb. The appearances of these lamps are highly appreciated as they look very decorative.

In view of the recent development in the world concerning the global pandemic, disinfection has become a topic of renewed interest as the demand for sterilization increases. One way of disinfecting involves the use of UV light. As a response to pathogenic outbreaks involving airborne microorganisms it would be beneficial to employ UV light for disinfecting air and objects at locations where the transmission of such microorganisms is believed to occur.

Disinfecting luminaires are used to flood spaces such as hospital rooms with UV-A (ultra-violet light of 315-380 nanometer (nm)), UV-B (ultra-violet light of 280-315 nanometer (nm)) and UV-C (ultra-violet light of 100-280 nm) radiation for disinfection purposes. Such disinfecting luminaires require a relatively brief time, e.g. several minutes, to achieve adequate disinfection but require the room to be evacuated of people. Another type of disinfecting luminaire uses violet light (i.e. 380-420 nm) and in particular a fixed 405 nm violet light source to provide disinfection without evacuating people from the room. Such luminaires may require hours to achieve adequate disinfection since violet light is less effective at killing pathogens compared to UV-B and UV-C radiation, and since the light dispersed over a wide area such that the irradiance level is relatively low.

In view of the above, it is desired to obtain a LED filament having an appealing aesthetic appearance and providing efficient and safe disinfection.

SUMMARY

In view of the above discussion, the purpose of the present invention is to provide a LED filament which has disinfecting properties.

The present invention thus provides a light-emitting diode (LED) filament configured to provide LED filament light. The LED filament comprises an elongated carrier comprising a first surface and a second surface arranged opposite to the first surface. The first and the second surfaces may be substantially parallel to each other.

The term "elongated carrier" means a substrate having a longitudinal extension and a width, such that the longitudinal extension is greater than the width. Preferably, the elongated carrier according to the present invention is in the form of a rectangular elongated strip.

The elongated carrier may be formed of rigid materials e.g. glass, ceramic, sapphire, or quartz, or formed of flexible materials, e.g. polymer such as polyamide. Preferably, the elongated carrier of the present invention is flexible. By the term "flexible" is meant that the elongated carrier may be arranged into different shapes by bending, folding, twisting, or any combination thereof. Further, the term "flexible" means that the shape of the elongated carrier may be malleable or adaptable. In particular, the elongated carrier may be formed into a spiral or helical shape, thus resembling an incandescent light bulb, as will be described in greater detail below.

The LED filament according to the present invention further comprises a plurality of first light-emitting diodes, LEDs, distributed along the first surface of the elongated carrier. The plurality of first LEDs is configured to emit a first LED light having a dominant peak wavelength within a first wavelength range.

The term "LED" as used in the context of the present invention implies any type of LED known in the art, such as inorganic LED(s), organic LED(s), polymer/polymeric LEDs, violet LEDs, blue LEDs, optically pumped phosphor coated LEDs, optically pumped nano-crystal LEDs. As used herein, the term "LED" can encompass a bare LED die arranged in a housing, which may be referred to as a LED package.

The plurality of first LEDs may be evenly distributed along the entire length of the first surface of the elongated carrier. By the expression "evenly distributed" is meant that the number of first LEDs per area unit of the first surface of the elongated carrier is constant along the entire length of the elongated carrier.

In particular, the plurality of first LEDs may be arranged as a single linear array, such as a single straight column. In such an embodiment, the LED filament may be slim, while providing a possibility to arrange LEDs emitting different colors and/or color temperatures. Further, the plurality of first LEDs may be arranged as a wave-shaped line, a zig-zag line, or the like.

Alternatively, the plurality of first LEDs may be arranged as several linear arrays, preferably being parallel to each other. Further, the plurality of first LEDs may be distributed in any other ordered pattern, such as stars, triangles, circles, or the like, or may be randomly distributed along the elongated carrier.

It is further conceivable to provide the plurality of first LEDs being arranged as a combination of at least two of the above-mentioned distribution patterns. In other words, a first subset of first LEDs of the plurality of first LEDs may be arranged in a first distribution pattern, thus forming a first LED filament section, and a second subset of first LEDs of the plurality of first LEDs may be arranged in a second distribution pattern, thus forming a second LED filament section. The LED filament may comprise a plurality of the first and second LED filament sections alternatingly arranged in a succession along the LED filament. When the LED filament is arranged in a substantially spiral shape, the first LED filament sections may be parallel to each other, and the second LED filament sections may be parallel to each other. The plurality of first LEDs may comprise at least 10 first LEDs, preferably at least 20 first LEDs, more preferably at least 30 first LEDs.

The LED filament according to the present invention further comprises a plurality of second light-emitting diodes, LEDs, distributed along the second surface of the elongated carrier, the plurality of second LEDs being configured to emit a second LED light having a dominant peak wavelength within a second wavelength range being different from the first wavelength range. The LED filament light may thus comprise the first LED light, the second LED light or combination thereof.

The first LED light may be white light. The white light has preferably a color temperature in a range from 2000 to 8000 K. The white light may have a CRI of at least 80, preferably at least 85. The plurality of first LEDs may comprise blue, green and/or red LEDs. Alternatively, or in addition, phosphor converted white LEDs may be used.

The plurality of second LEDs may be evenly distributed along the entire length of the second surface of the elongated carrier. By the expression "evenly distributed" is meant that the number of second LEDs per area unit of the second surface of the elongated carrier is constant along the entire length of the elongated carrier.

In particular, the plurality of second LEDs may be arranged as a single linear array, such as a single straight column. In such an embodiment, the LED filament may be slim, while providing a possibility to arrange LEDs emitting different colors and/or color temperatures. Further, the plurality of second LEDs may be arranged as a wave-shaped line, a zig-zag line, or the like.

Alternatively, the plurality of second LEDs may be arranged as several linear arrays, preferably being parallel to each other. Further, the plurality of second LEDs may be distributed in any other ordered pattern, such as stars, triangles, circles, or the like, or may be randomly distributed along the elongated carrier.

It is further conceivable to provide the plurality of second LEDs being arranged as a combination of at least two of the above-mentioned distribution patterns. In other words, a first subset of second LEDs of the plurality of second LEDs may be arranged in a first distribution pattern, thus forming a first LED filament section, and a second subset of second LEDs of the plurality of second LEDs may be arranged in a second distribution pattern, thus forming a second LED filament section. The LED filament may comprise a plurality of the first and second LED filament sections alternatingly arranged in a succession along the LED filament. When the LED filament is arranged in a substantially spiral shape, the first LED filament sections may be parallel to each other, and the second LED filament sections may be parallel to each other.

According to the present invention, the first wavelength range is in the visible wavelength range and the second wavelength range is in the UV wavelength range and/or violet wavelength range. Thus, the LED filament of the present invention combines aesthetically appealing properties with disinfection function. Such a LED filament may be used in a conventionally shaped light bulbs normally used in homes and other facilities where the appearance of a light source is important, while providing disinfection of the air within the facility. In the context of the present invention, the violet wavelength range may be in a range from 380 nm to 420 nm, the UV wavelength range may be from 100 nm to 380 nm, and the visible wavelength range may be from 420 nm to 800 nm.

As mentioned above, the second LED light may be only in the UV wavelength range and not the violet wavelength range. Preferably, the second LED light is in the UV-C and/or UV-B wavelength range, such that both viruses and bacteria is inactivated, since UV-A and violet light only inactivate bacteria. As mentioned above, UV-B wavelength range may be from 280 nm to 315 nm, and UV-C wavelength range may be from 100 to 280 nm. The disinfection performance of UV-C light is higher than the disinfection performance of UV-B light. UV-B light has the additional benefit of assisting in formation of cholecalciferol (vitamin D3) in human skin that is exposed. More preferably, the second LED light is only in the UV-C wavelength range. Most preferably, the second LED light is only in the far UV-C wavelength range, i.e. from 190 nm to 230 nm, because this type of UV light is more safe to humans than light in the near UV-C wavelength range, e.g. the second LED light having a dominant peak wavelength at 225 nm.

The first LED light may be within the first wavelength range or may comprise components being outside the first wavelength range. Further, the second LED light may be within the second wavelength range or may comprise components being outside the second wavelength range.

It may be desirable that the plurality of first LEDs provides a first LED light being perceived as a line/filament emission. On the other hand, violet, and in particular UV LEDs are very expensive, and it is therefore advantageous to minimize the number of the seconds LEDs. To this end, the plurality of first LEDs may have a pitch $P_1$, and the plurality of second LEDs may have a pitch $P_2$, wherein $P_2 > 2 \cdot P_1$, preferably $P_2 > 3 \cdot P_1$, more preferably $P_2 > 4 \cdot P_1$, most preferably $P_2 > 5 \cdot P_1$. In the context of the present invention, the term "pitch" is defined as the centre-to-centre distance between each two LEDs on the flexible printed circuit board (FPCB). Thus, the number of second LEDs in the plurality of seconds LEDs may be significantly lower than the number of first LEDs in the plurality of first LEDs, thus providing a relatively low cost filament. In particular, the number of second LEDs in the plurality of second LEDs may be less than nine.

The plurality of first LEDs may comprise n first LEDs, and the plurality of second LEDs may comprise m second LEDs, where $n > m$. Preferably, $n > 2 \cdot m$, more preferably, $n > 3 \cdot m$, most preferably, $n > 4 \cdot m$.

The second LED light in the form of UV light may excite and/or degrade the phosphor that is present in the first LEDs. In order to avoid such an unwanted effect, the elongated carrier may be reflective. In particular, the elongated carrier may have reflectivity of at least 70%, preferably at least 75%, more preferably at least 80%, most preferably at least 85%. In particular, the elongated carrier may have a low transmittance of light of less than 20%, preferably less than 15%, more preferably less than 10%, most preferably less than 5%.

The LED filament according to the present invention may be arranged such that at least one second LED of the plurality of second LEDs is emitting second LED light in a first direction and at least one second LED of the plurality of second LEDs is emitting second LED light in a second direction being opposite to the first direction. Such an embodiment may be achieved when the LED filament is arranged into a spiral or helix as will be described in greater detail below.

The LED filament according to the present invention may be arranged such that at least one second LED of the plurality of second LEDs is emitting second LED light in a third direction being perpendicular to the first and the second directions and at least one second LED of the plurality of second LEDs is emitting second LED light in a fourth direction being opposite to the third direction. In such an embodiment, omnidirectional disinfecting light is emitted by the LED filament.

As mentioned above, it is preferred to optimize the number of second LEDs such that efficient disinfection is provided while manufacturing cost is minimized. To this end, the plurality of second LEDs may be arranged on a portion of the second surface of the elongated carrier. The portion may be from ⅙ to ½ of the longitudinal extension of the second surface of the elongated carrier. Preferably, the plurality of second LED is arranged on a portion being less than ⅓ of the longitudinal extension of the second surface of the elongated carrier.

The elongated carrier of the LED filament is arranged to support the plurality of first LEDs and the plurality of second LEDs. Moreover, the elongated carrier may comprise electrodes for electrically connecting the at least one first LED of the plurality of first LEDs and the at least one second LED of the plurality of second LEDs. The plurality of first LEDs and the plurality of second LEDs may be mechanically coupled to the substrate. A controller may be provided for controlling the plurality of first LEDs and/or the plurality of second LEDs. In particular, the plurality of first LEDs and the plurality of second LEDs may be controlled individually. In other words, the user may actively select whether a visible LED light, a disinfecting LED light or both visible and disinfecting LED light are emitted by the LED filament. Further, each first LED of the plurality of first LEDs may be controlled individually and/or each second LED of the plurality of second LEDs may be controlled individually. The plurality of first LEDs may comprise LEDs having different colors and/or different color temperatures.

At least 50%, preferably at least 60%, more preferably at least 70%, most preferably at least 80% of the elongated carrier is free from LEDs, electrodes and/or other components. In other words, less than 50%, preferably less than 40%, more preferably less than 30% and most preferably less than 20% of the elongated carrier comprises LEDs, electrodes and/or other components.

The plurality of first LEDs may be encapsulated or covered by a first encapsulant comprising a luminescent material and/or scattering material. The luminescent material may be phosphor, in particular inorganic phosphor, and may be configured to at least partially convert the first LED light into a first converted light. For example, the first LED light may be blue light and the luminescent material may at least partly converts the blue light into green/yellow and/or red converted light. The first LED light and/or the converted light may be white light. The white light may have a colour temperature in a range from 2000 to 8000 K. The white light may have a CRI of at least 80 and preferably at least 85.

Further, the plurality of second LEDs may be free from an encapsulant or may be encapsulated of covered by a second encapsulant being at least partially light-transmissive, preferably translucent, and more preferably transparent. The second encapsulant may have a transmittance of at least 50%, preferably at least 65%, more preferably at least 75%. According to such an embodiment, a LED filament having an improved lifetime is obtained, since the amount of UV light impinging the elongated carrier is reduced.

The first and/or the second encapsulant may comprise or consist of polysiloxane.

By the term "encapsulate" is meant to surround, encapsulate and/or enclose at least partially. By the term "translucent" in the context of the present invention is meant a material allowing light to pass through, wherein the photons can be scattered at either of the two interfaces or internally.

The plurality of first LEDs and the plurality of second LEDs may be arranged on the same substrate. The substrate may be a printed circuit board (PCB) and may be folded and/or bended.

As mentioned above, the LED filament according to the present invention may be arranged in a spiral or helix having a central axis in order to provide attractive aesthetical appearance of the LED filament. It should be noted that when the LED filament is arranged in a spiral or helical shape, a spiral or a helix comprising the LED filament is formed. The spiral has a longitudinal extension along a central axis, an outer surface facing away from the central axis, and an inner surface facing the central axis. The central axis may be the longitudinal axis of e.g. a lamp. The spiral comprises a first end portion and a second end portion spaced apart along the central axis of the spiral, and a middle portion arranged between the first and the second end portions. The spiral comprising the LED filament may be arranged such that the central axis is oriented vertically. The spiral may further comprise a plurality of loops.

Preferably, the first surface of the LED filament constitutes the outer surface of the spiral. In other words, the first surface of the elongated carrier may face away from the central axis of the spiral and the second surface may face towards the central axis of the spiral. Such an embodiment brings the advantage of providing a large distance between the second LEDs and the observer, thus decreasing the intensity of the disinfecting second LED light, and providing improved safety. Further, in such a configuration, the elongated carrier may have a shielding function to shield the first LEDs and/or encapsulant comprising scattering/luminescent material from the potentially damaging second LED light. The first LED light from the LED filament may be spiral shaped light.

Alternatively, the first surface of the elongated carrier may face towards the central axis of the spiral and the second surface may face away from the central axis of the spiral. In such an embodiment, the distance between the second LEDs and illuminated space is rather short, such that the light the disinfecting second LED light is not blocked by the elongated carrier, which provides improved disinfection efficiency.

In order to provide an improved shielding from the second LED light, the second LEDs may be arranged in the middle portion of the spiral, while the first and the second end portions may be substantially free from the second LEDs. Further, it is conceivable that the second LEDs are arranged on predefined loops, while the other loops are substantially free from the second LEDs.

The present invention further relates to a lamp or a luminaire comprising a LED filament as described above and a light exit window. As mentioned above, it is desirable to provide a lamp or a luminaire resembling an incandescent light bulb. To this end, the LED filament may be arranged in a spiral or helical shape.

The luminaire may comprise a housing comprising a light exit window arranged such that the outer surface of the spiral constituted by the first or the second surface of the elongated carrier faces the light exit window. By such an arrangement, the LED filament light comprising or consisting of visible LED light and/or disinfecting LED light will be emitted through the light exit window. The luminaire may further comprise a mounting means for mounting the luminaire to a wall or a ceiling. The lamp may further comprise a cap, an envelope, a driver and/or a controller. The cap and/or the envelope may at least partially enclose the LED filament.

BRIEF DESCRIPTION OF THE DRAWINGS

Embodiments of the invention will now be described by way of example with reference to the accompanying drawings, of which.

Figure 1:
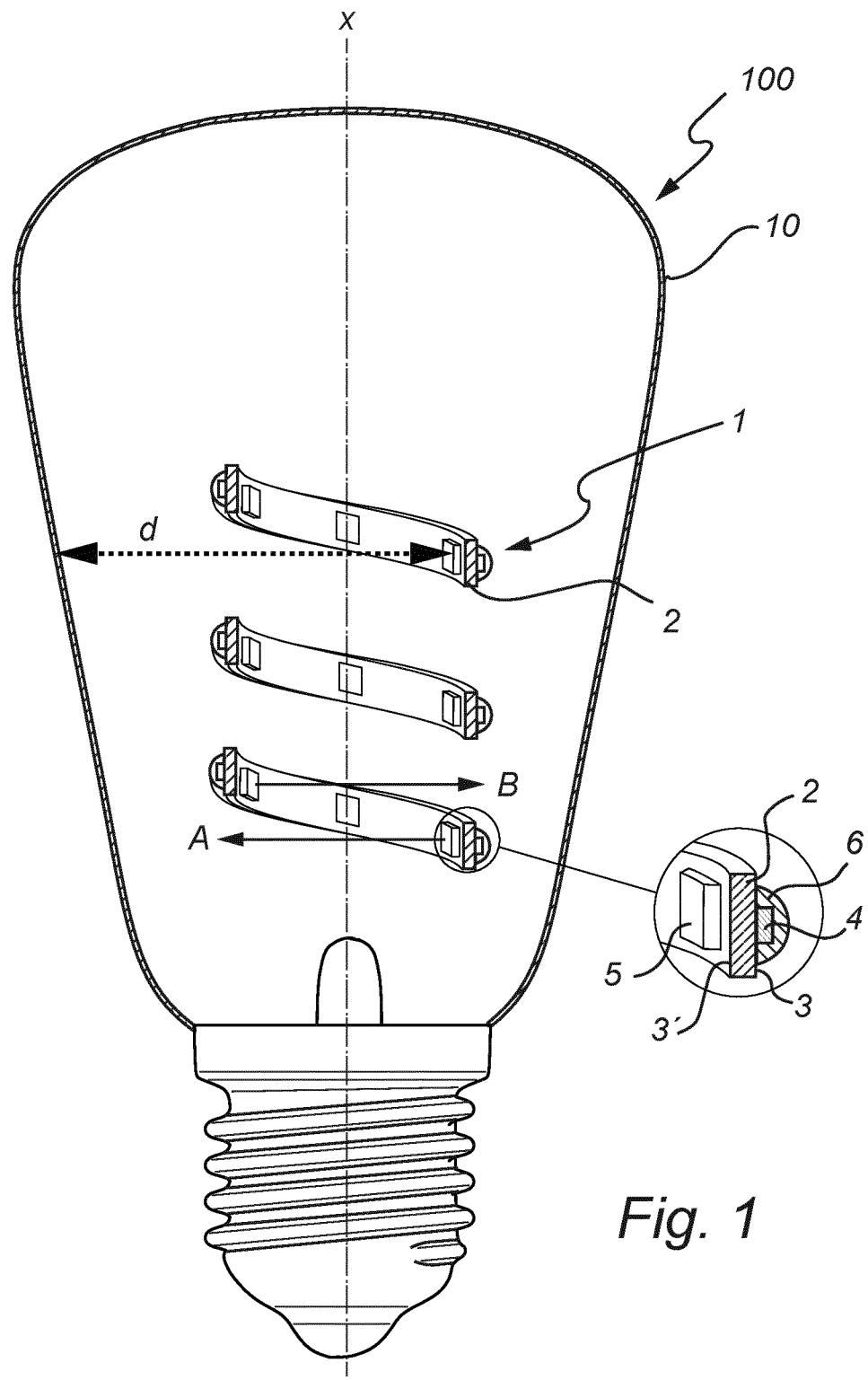
FIG. 1 shows a cross-sectional view of a lamp comprising a LED filament according to exemplifying embodiment of the present invention.

All the figures are schematic, not necessarily to scale, and generally only show parts which are necessary in order to elucidate embodiments of the present invention, wherein other parts may be omitted or merely suggested.

DETAILED DESCRIPTION

The present invention will now be described hereinafter with reference to the accompanying drawings, in which exemplifying embodiments of the present invention are shown. The present invention may, however, be embodied in many different forms and should not be construed as limited to the embodiments of the present invention set forth herein; rather, these embodiments of the present invention are provided by way of example so that this disclosure will convey the scope of the invention to those skilled in the art. In the drawings, identical or similar reference numerals denote the same or similar components having a same or similar function, unless specifically stated otherwise.

FIG. 1 illustrates a light-emitting diode (LED) filament 1 configured to provide LED filament light. The LED filament 1 comprises an elongated carrier 2 comprising a first surface 3 and a second surface 3' arranged opposite to the first surface 3. The first and the second surfaces 3, 3' are substantially parallel to each other.

As may be seen in FIG. 1, the elongated carrier 2 is in the form of a rectangular elongated strip. The elongated carrier 2 is flexible and is formed into a spiral or helical shape, thus resembling an incandescent light bulb.

The LED filament 1 comprises a plurality of first light-emitting diodes 4, LEDs, distributed along the first surface 3 of the elongated carrier 2. The plurality of first LEDs 4 is configured to emit a first LED light having a dominant peak wavelength within a first wavelength range. The plurality of first LEDs 4 is evenly distributed along the entire length of the first surface 3 of the elongated carrier 2 and is arranged as a single linear array.

The LED filament 2 further comprises a plurality of second light-emitting diodes 5, LEDs, distributed along the second surface 3' of the elongated carrier 2, the plurality of second LEDs 5 being configured to emit a second LED light having a dominant peak wavelength within a second wavelength range being different from the first wavelength range. The LED filament light may thus comprise the first LED light, the second LED light or combination thereof.

The plurality of second LEDs 5 is evenly distributed along the entire length of the second surface 3' of the elongated carrier 2 and is arranged as a single linear array.

The first wavelength range is in the visible wavelength range and the second wavelength range is in the UV wavelength range and/or violet wavelength range. Thus, the LED filament of the present invention combines aesthetically appealing properties with disinfection function. Such a LED filament may be used in a conventionally shaped light bulbs normally used in homes and other facilities where the appearance of a light source is important, while providing disinfection of the air within the facility.

It is desirable that the plurality of first LEDs 4 provides a first LED light being perceived as a line/filament emission. On the other hand, violet, and in particular UV LEDs are very expensive, and it is therefore advantageous to minimize the number of the seconds LEDs 5. To this end, the plurality of first LEDs 4 has a pitch $P_1$, and the plurality of second LEDs 5 has a pitch $P_2$, wherein $P_2 > 2 \cdot P_1$. In the context of the present invention, the term "pitch" is defined as the centre-to-centre distance between each two LEDs on the flexible printed circuit board (FPCB). Thus, the number of second LEDs in the plurality of seconds LEDs 5 may be significantly lower than the number of first LEDs in the plurality of first LEDs 4.

The LED filament 1 is arranged such that at least one second LED of the plurality of second LEDs 5 is emitting second LED light in a first direction A and at least one second LED of the plurality of second LEDs 5 is emitting second LED light in a second direction B being opposite to the first direction A.

The LED filament 1 is further arranged such that at least one second LED of the plurality of second LEDs 5 is emitting second LED light in a third direction C (not shown, directed away from the viewer of FIG. 1) being perpendicular to the first and the second directions A, B, and at least one second LED of the plurality of second LEDs 5 is emitting second LED light in a fourth direction D being opposite to the third direction C (not shown, directed towards the viewer of FIG. 1). In such an embodiment, omnidirectional disinfecting light is emitted by the LED filament 1.

The plurality of first LEDs 1 is encapsulated or covered by a first encapsulant 6 comprising a luminescent material and/or scattering material. It should be noted that the encapsulant 6 is omitted in FIG. 2. The plurality of second LEDs 5 is free from an encapsulant.

Figure 2:
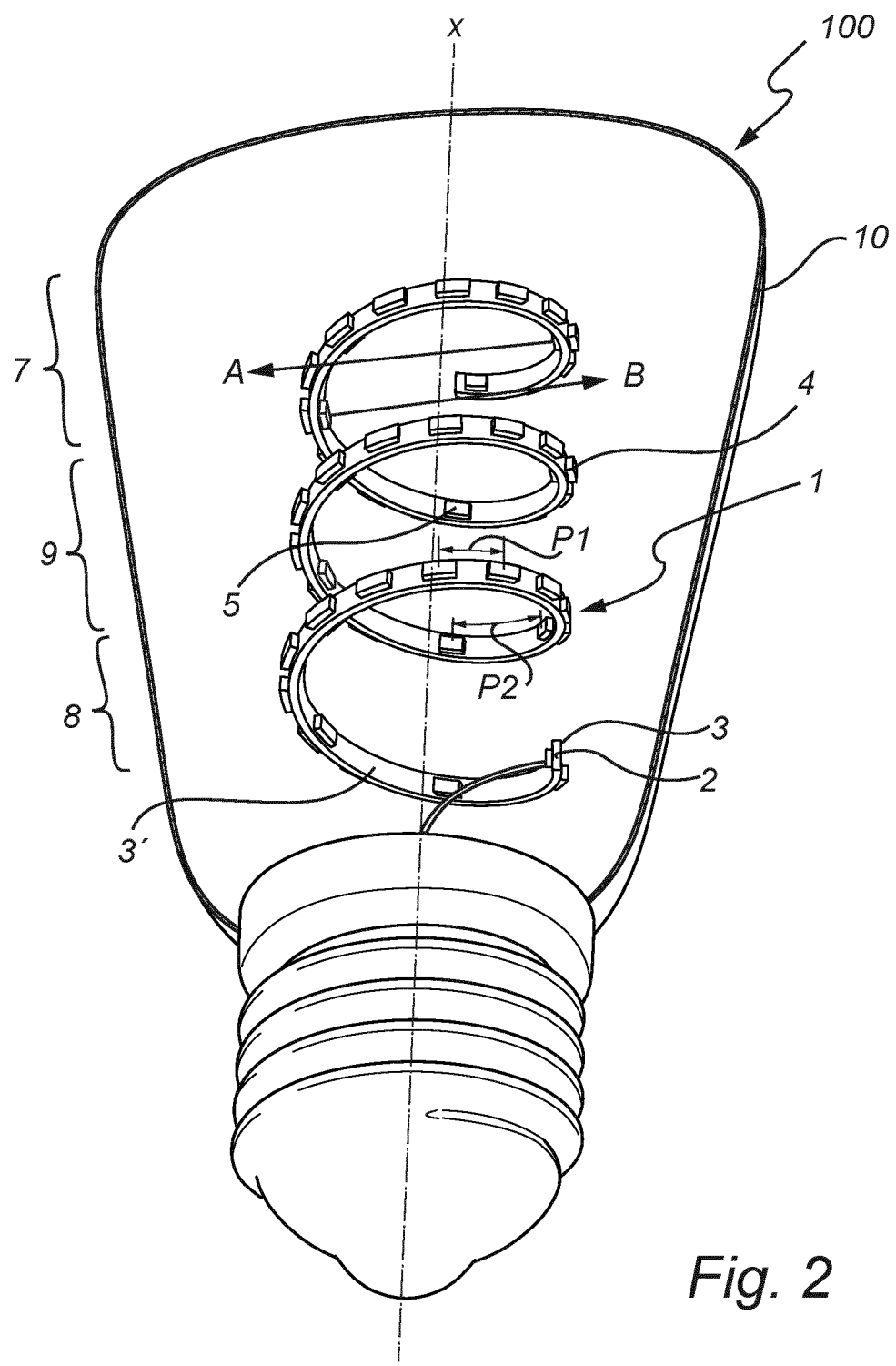
FIG. 2 illustrates a perspective view of the lamp depicted in FIG. 1.

As may be seen in FIGS. 1 and 2, the LED filament 1 is arranged in a spiral or helix in order to provide attractive aesthetical appearance of the LED filament 1. The spiral has a longitudinal extension along a central axis X, an outer surface facing away from the central axis X, and an inner surface facing the central axis X. The spiral comprises a first end portion 7 and a second end portion 8 spaced apart along the central axis X of the spiral, and a middle portion 9 arranged between the first and the second end portions 7, 8. The spiral comprising the LED filament 1 is arranged such that the central axis X is oriented vertically. The spiral further comprises a plurality of loops.

As may be gleaned from FIGS. 1 and 2, the first surface 3 of the LED filament 1 constitutes the outer surface of the spiral. In other words, the first surface 3 of the elongated carrier 2 faces away from the central axis X of the spiral and the second surface 3' faces towards the central axis of the spiral. Such an embodiment brings the advantage of providing a large distance d between the second LEDs and the observer, thus decreasing the intensity of the disinfecting second LED light, and providing improved safety.

FIGS. 1 and 2 depicts a lamp 100 comprising a LED filament 1 as described above and a light exit window 2. As mentioned above, the lamp 100 resembles an incandescent light bulb. The outer surface of the spiral constituted by the first surface 3 of the elongated carrier 2 faces the light exit window 10.

Although the present invention has been described with reference to various embodiments, those skilled in the art will recognize that changes may be made without departing from the scope of the invention. It is intended that the detailed description be regarded as illustrative and that the appended claims including all the equivalents are intended to define the scope of the invention. While the present invention has been illustrated in the appended drawings and the foregoing description, such illustration is to be considered illustrative or exemplifying and not restrictive; the present invention is not limited to the disclosed embodiments. Other variations to the disclosed embodiments can be understood and effected by those skilled in the art in practicing the claimed invention, from a study of the drawings, the disclosure, and the appended claims. In the appended claims, the word "comprising" does not exclude other elements or steps, and the indefinite article "a" or "an" does not exclude a plurality. The mere fact that certain measures are recited in mutually different dependent claims does not indicate that a combination of these measures cannot be used to advantage. Any reference signs in the claims should not be construed as limiting the scope.

The invention claimed is:

1. A light-emitting diode (LED) filament configured to provide LED filament light and comprising:
    an elongated carrier comprising a first surface and a second surface arranged opposite to said first surface;
    a plurality of first light-emitting diodes, LEDs, distributed along said first surface of said elongated carrier, said plurality of first LEDs being configured to emit a first LED light having a dominant peak wavelength within a first wavelength range;
    a plurality of second light-emitting diodes, LEDs, distributed along said second surface of said elongated carrier, said plurality of second LEDs being configured to emit a second LED light having a dominant peak wavelength within a second wavelength range being different from said first wavelength range,
    wherein said LED filament is arranged in a spiral or helix having a central axis,
    wherein said first wavelength range is in the visible wavelength range and said second wavelength range is in the UV wavelength range and/or violet wavelength range, and
    wherein said plurality of first LEDs is encapsulated or covered by a first encapsulant comprising a luminescent material and/or scattering material, and wherein said plurality of second LEDs is free from an encapsulant or is encapsulated of covered by a second encapsulant being transparent.

2. The LED filament according to claim 1, wherein said first LED light is within said first wavelength range, and/or wherein said second LED light is within said second wavelength range.

3. The LED filament according to claim 1, wherein said UV wavelength range is in the UV-C and/or UV-B wavelength range.

4. The LED filament according to claim 1, wherein said plurality of first LEDs has a pitch $P_1$, wherein said plurality of second LEDs has a pitch $P_2$, and wherein $P_2 > 2 \cdot P_1$.

5. The LED filament according to claim 1, wherein said elongated carrier is reflective.

6. The LED filament according to claim 1, wherein at least one second LED of said plurality of second LEDs is emitting second LED light in a first direction and at least one second LED of said plurality of second LEDs is emitting second LED light in a second direction being opposite to said first direction.

7. The LED filament according to claim 6, wherein at least one second LED of said plurality of second LEDs is emitting second LED light in a third direction being perpendicular to said first and said second directions and at least one second LED of said plurality of second LEDs is emitting second LED light in a fourth direction being opposite to said third direction.

8. The LED filament according to claim 1, wherein said plurality of second LED is arranged on a portion of said second surface of said elongated carrier, wherein said portion is from ⅙ to ½ of the longitudinal extension of said second surface of said elongated carrier.

9. The LED filament according to claim 1, wherein said plurality of first LEDs and said plurality of second LEDs are arranged on the same substrate, and wherein said substrate is folded and/or bended.

10. The LED filament according to claim 1, wherein said first surface of said elongated carrier faces away from said central axis of said spiral and said second surface of said elongated carrier faces towards said central axis of said spiral.

11. The LED filament according to claim 1, wherein said first surface of said elongated carrier faces towards said central axis of said spiral and said second surface of said elongated carrier faces away from said central axis of said spiral.

12. A lamp or a luminaire comprising a LED filament according to claim 1 and a light exit window.

13. A lamp or luminaire according to claim 12,
    wherein said second LED light is within said second wavelength range;
    wherein said second wavelength range is in the UV wavelength range;
    wherein at least one second LED of said plurality of second LEDs is emitting second LED light in a first direction and at least one second LED of said plurality of second LEDs is emitting second LED light in a second direction being opposite to said first direction;
    wherein at least one second LED of said plurality of second LEDs is emitting second LED light in a third direction being perpendicular to said first and said second directions and at least one second LED of said plurality of second LEDs is emitting second LED light in a fourth direction being opposite to said third direction;
    wherein said LED filament is arranged in a spiral or helix having a central axis.

* * * * *